United States Patent
Quinones-Garcia et al.

(10) Patent No.: US 10,695,395 B2
(45) Date of Patent: Jun. 30, 2020

(54) COLLAGEN 7 COMPOSITIONS AND METHODS OF USING THE SAME

(71) Applicant: SHIRE HUMAN GENETIC THERAPIES, INC., Lexington, MA (US)

(72) Inventors: Igor Quinones-Garcia, Lexington, MA (US); Lin Guey, Lexington, MA (US); Kris Lowe, Lexington, MA (US); Vinh Nguyen, Lexington, MA (US); Bing He, Lexington, MA (US); Amey Bandekar, Lexington, MA (US); Sujit Basu, Lexington, MA (US)

(73) Assignee: PHOENIX TISSUE REPAIR, INC., Boston, MA (US)

( * ) Notice: Subject to any disclaimer, the term of this patent is extended or adjusted under 35 U.S.C. 154(b) by 0 days.

(21) Appl. No.: 16/065,512

(22) PCT Filed: Dec. 21, 2016

(86) PCT No.: PCT/US2016/067995
§ 371 (c)(1),
(2) Date: Jun. 22, 2018

(87) PCT Pub. No.: WO2017/112757
PCT Pub. Date: Jun. 29, 2017

(65) Prior Publication Data
US 2019/0000912 A1   Jan. 3, 2019

Related U.S. Application Data

(60) Provisional application No. 62/293,209, filed on Feb. 9, 2016, provisional application No. 62/278,816, filed on Jan. 14, 2016, provisional application No. 62/387,241, filed on Dec. 23, 2015.

(51) Int. Cl.
| | | |
|---|---|---|
| A61K 38/01 | (2006.01) | |
| A61Q 19/08 | (2006.01) | |
| A61K 8/65 | (2006.01) | |
| A61K 8/60 | (2006.01) | |
| A61K 38/39 | (2006.01) | |
| C07K 14/78 | (2006.01) | |
| A61K 8/44 | (2006.01) | |
| A61K 8/20 | (2006.01) | |
| A61K 8/49 | (2006.01) | |
| A61K 8/24 | (2006.01) | |
| A61K 9/00 | (2006.01) | |
| A61P 17/02 | (2006.01) | |
| A61K 47/10 | (2017.01) | |
| A61K 47/18 | (2017.01) | |
| A61K 47/26 | (2006.01) | |

(52) U.S. Cl.
CPC ............. *A61K 38/014* (2013.01); *A61K 8/20* (2013.01); *A61K 8/24* (2013.01); *A61K 8/44* (2013.01); *A61K 8/4993* (2013.01); *A61K 8/60* (2013.01); *A61K 8/65* (2013.01); *A61K 9/0019* (2013.01); *A61K 38/39* (2013.01); *A61P 17/02* (2018.01); *A61Q 19/08* (2013.01); *C07K 14/78* (2013.01); *A61K 47/10* (2013.01); *A61K 47/183* (2013.01); *A61K 47/26* (2013.01)

(58) Field of Classification Search
CPC ...... A61K 38/014; A61K 38/39; A61K 47/10; A61K 47/183; A61K 47/26; A61K 8/20; A61K 8/24; A61K 8/44; A61K 8/4993; A61K 8/60; A61K 8/65; A61K 9/0019; A61P 17/02; A61Q 19/08; C07K 14/78
See application file for complete search history.

(56) References Cited

U.S. PATENT DOCUMENTS

| | | |
|---|---|---|
| 7,816,495 B2 | 10/2010 | Kingsland et al. |
| 2003/0096973 A1 | 5/2003 | Gruber et al. |
| 2008/0038753 A1 | 2/2008 | Branum et al. |
| 2011/0182962 A1 | 7/2011 | Mckay |
| 2012/0121580 A1 | 5/2012 | Bhambhani et al. |
| 2014/0186351 A1 | 7/2014 | Britta et al. |
| 2018/0104186 A1* | 4/2018 | Badiavas .............. A61K 45/06 |
| 2019/0077845 A1* | 3/2019 | Quinones-Garcia ... C07K 14/78 |

FOREIGN PATENT DOCUMENTS

WO    2015157469 A2    10/2015

OTHER PUBLICATIONS

Pramanick et al. Excipient Selection in Parenteral Formulation Development. Pharma Times • vol. 65, No. 3, Mar. 2013, pp. 65-77. (Year: 2013).*
Phosphate-Buffered Saline (PBS). Cold Spring Harb Protoc 2006. 2006: pdb.rec8247-2006 Cold Spring Harbor Laboratory Press, 1 page. accessed online at http://cshprotocols.cshlp.org/content/2006/1/pdb.rec8247 on Dec. 4, 2019. (Year: 2006).*
Woodley et al. Intravenously Injected Recombinant Human Type VII Collagen Homes to Skin Wounds and Restores Skin Integrity of Dystrophic Epidermolysis Bullosa. J Invest Dermatol, Jul. 2013, vol. 133, No. 7, pp. 1910-1913. (Year: 2013).*
Chen, Mei, et al. The Recombinant Expression of Full-length Type VII Collagen and Characterization of Molecular Mechanisms Underlying Dystrophic Epdermolysis Bullosa, The Journal of Biological Chemistry, vol. 277, No. 3, Issue of Jan. 18, 2002, pp. 2118-2124.
Ohtake, S et al. "Interactions of formulation excipients with proteins in solution and in the dried state." Advanced Drug Delivery Reviews, 2011. vol. 63. No. 1.

(Continued)

*Primary Examiner* — Marcela M Cordero Garcia
(74) *Attorney, Agent, or Firm* — Donna T. Ward; Lingyun Jia; DT Ward, PC (57) ABSTRACT

The present disclosure relates to compositions comprising collagen 7 and methods of using the same to treat DEB.

18 Claims, 6 Drawing Sheets

(56) References Cited

OTHER PUBLICATIONS

International Search Report & Written Opinion dated Feb. 28, 2017 in co-pending application No. PCT/US2016/067995, entitled Collagen 7 Compositions and Methods of Using the Same.
Extended European Search Report received in corresponding EP application No. 16880019.1 dated Jul. 12, 2019.
Remington J et al: "Injection of recombinant human type VII collagen corrects the disease phenotype in a murine model of dystrophic epidermolysis bullosa", Molecular Therapy, Nature Publishing Group, GB, vol. 17, No. 1, Jan. 17, 2009.

* cited by examiner

COLLAGEN 7 COMPOSITIONS AND METHODS OF USING THE SAME

CROSS REFERENCE TO RELATED APPLICATIONS

This application is a 35 U.S.C. § 371 U.S. National Stage Entry of International Application No. PCT/US2016/067995 filed Dec. 21, 2016, which claims priority to U.S. provisional patent application No. 62/387,241 filed Dec. 23, 2015, U.S. provisional patent application No. 62/278,816, filed Jan. 14, 2016 and U.S. provisional patent application No. 62/293,209, filed Feb. 9, 2016; the contents of each of which are herein incorporated by reference in their entireties.

FIELD

The present invention relates to compositions (e.g., pharmaceutical compositions) and more particularly, to collagen 7 compositions and methods of using the same to treat dystrophic epidermolysis bullosa.

BACKGROUND

The collagen VII (C7) protein is a structural protein in which C7 is both a structural and functional precursor for the formation of anchoring fibrils which enable the attachment of the epidermis and the dermis. The C7 monomer assembles as a homotrimer of approximately 900 kDa, containing one NC-1 and one NC-2 binding region. The homotrimer is held together via an alpha helical coil. From a homotrimer, these C7 protein precursors align into an anti-parallel dimer with an increase in molecular weight to 1.8 mDa. Lateral assembly of anti-parallel dimers leads to the formation of the anchoring fibrils. The rC7 protein demonstrates "stickiness," and the propensity to precipitate at higher protein concentrations, particularly in PBS buffer.

Lack of C7 leads to abnormal decrease in these anchoring fibrils and a condition known as Dystrophic Epidermolysis Bullosa (DEB). EB encompasses a group of molecularly diverse diseases characterized by the development of blisters after minor mechanical trauma to the skin. (1) Severity, extracutaneous manifestations and clinical course depend on the type of EB; however, almost all patients experience blistering or ruptured skin. (2)

Dystrophic epidermolysis bullosa (DEB) is a form of EB characterized by development of scarring with healing. (3) In patients with DEB, blistering can be triggered by even minor mechanical trauma owing to the extremely fragile nature of the skin. This leads to a chronic cycle of blistering, healing, and reblistering that causes patients to suffer from painful wounds and debilitating scarring of epithelial tissue. There is no cure for DEB and management focuses on supportive care.

Dystrophic EB is caused by mutations in the Col7a1 gene, which encodes the alpha chain of collagen VII (C7), a protein essential for the formation of the anchoring fibrils that anchor the basement membrane to the underlying dermis. (4) The condition is inherited as either a dominant form (DDEB) or a recessive form (RDEB), with RDEB typically having a more severe phenotype. (5)

The DEB mouse model (Col7a1−/−) has a targeted inactivation of the Col7a1 gene, resulting in severe blistering that mimics the histological and ultrastructural presentation of severe human RDEB. (6) These mice have no detectable collagen VII at the dermal-epidermal basement membrane zone (BMZ), completely lack anchoring fibrils, and are born with extensive cutaneous blisters on their ventral surface and hemorrhagic blisters on their paws and neck, with mortality typically observed within the first week of life.

SUMMARY

The present disclosure relates to compositions comprising collagen 7 and methods of preparing such compositions. In certain embodiments, the composition comprises recombinant collagen 7, sodium phosphate, sodium citrate, sodium chloride, arginine, a sugar, and a surfactant. It is possible to exclude one or more of the sodium phosphate, sodium citrate, sodium chloride, arginine, sugar, or surfactant from the composition.

In certain embodiments, the sugar is sucrose. In certain embodiments the surfactant is a polysorbate, such as polysorbate 20 or polysorbate 80.

In certain embodiments, the sodium phosphate is present in an amount ranging from 100 mM to 1 mM, 50 mM to 5 mM, 25 mM to 5 mM, 10 mM to 5 mM, 10 mM to 1 mM or about 10 m M.

In certain embodiments, the sodium citrate is present in an amount ranging from 100 mM to 1 mM, 50 mM to 1 mM, 25 mM to 1 mM, 10 mM to 1 mM, 5 mM to 1 mM or about 5 mM.

In certain embodiments, the sodium chloride is present in an amount ranging from 200 mM to 10 mM, 100 mM to 20 mM, 80 mM to 50 mM, or about 70 mM.

In certain embodiments, the arginine is present in an amount ranging from 200 mM to 5 mM, 150 mM to 50 mM, 100 mM to 75 mM, or about 100 mM.

In certain embodiments, the sugar is present in an amount ranging from 100 mM to 10 mM, 100 mM to 50 mM, 75 mM to 35 mM, 60 mM to 40 mM, or about 50 mM. In certain embodiments, the sucrose is present in an amount ranging from 100 mM to 1 mM, 100 mM to 50 mM, 75 mM to 35 mM, 60 mM to 40 mM, or about 50 mM.

In certain embodiments, the surfactant is present in an amount ranging from 1% to 0.01%, 0.5% to 0.05%, 0.025% to 0.05%, 0.1% to 0.05%, 0.05% to 0.01% or about 0.05% (w/v). In certain embodiments, the polysorbate (e.g., polysorbate 20) is present in an amount ranging from 1% to 0.01%, 0.5% to 0.05%, 0.025% to 0.05%, 0.1% to 0.05%, 0.05% to 0.01% or about 0.05% (w/v).

In certain embodiments, the composition has a pH of between 8.0 to 6.0, 7.5 to 6.5, 7.5 to 7.0, 7.4 to 7.0, 7.3 to 7.0, 7.2 to 7.0, 7.1 to 7.0, 7.2 to 7.1, 7.2±0.3, about 7.1, or about 7.2

In certain embodiments, the composition comprises recombinant collagen 7, 100 mM to 10 mM sodium phosphate, 100 mM to 1 mM sodium citrate, 200 mM to 10 mM sodium chloride, 200 mM to 10 mM arginine, 100 mM to 10 mM sucrose, and 1.0% to 0.01% (w/v) polysorbate 20 and optionally a pH of 7.2 to 7.1.

In certain embodiments, the composition comprises recombinant collagen 7, 25 mM to 5 mM sodium phosphate, 25 mM to 1 mM sodium citrate, 100 mM to 20 mM sodium chloride, 150 mM to 50 mM arginine, 75 mM to 35 mM sucrose, and 0.5% to 0.05% polysorbate 20 (w/v) and optionally a pH of 7.2 to 7.1.

In one embodiment, the composition comprises recombinant collagen 7, about 10 mM sodium phosphate, about 5 mM sodium citrate, about 70 mM sodium chloride, about 100 mM arginine, about 50 mM sucrose, and about 0.05% polysorbate 20 (w/v) and has a pH of about 7.1.

In another embodiment, the composition comprises recombinant collagen 7, 10 mM sodium phosphate, 5 mM sodium citrate, 70 mM sodium chloride, 100 mM arginine, 50 mM sucrose, and 0.05% polysorbate 20 (w/v) and has a pH of 7.1.

In another embodiment, the composition comprises recombinant collagen 7, 10 mM sodium phosphate, 5 mM sodium citrate, 70 mM sodium chloride, 100 mM arginine, 50 mM sucrose, and 0.05% polysorbate 20 (w/v) and has a pH of 7.2±0.3.

In certain embodiments, the recombinant collagen 7 is a human collagen 7.

The collagen 7 compositions have increased stability. In certain embodiments, the composition is stable for 3 months following storage at −65±5° C. or −20±5° C. in a 1 liter polycarbonate bottle (500 mL of the composition). In certain embodiments, the composition is stable for 6 months following storage at −65±5° C. or −20±5° C. in a 10 cc glass vial (5.5 mL of composition). In certain embodiments, the composition is stable following storage for 2 weeks at 25±3° C. In certain embodiments, the composition is stable following storage for up to 1 month at 5±3° C.

The compositions may be pharmaceutical compositions comprising one or more additional pharmaceutical excipients that can be used, for example, to treat DEB.

Another aspect is directed to a method of treating DEB, the method comprising administering to a subject in need thereof an effective amount of a recombinant collagen 7 composition, as described herein.

The foregoing and other objects, features, and advantages of the rC7 compositions will become more apparent from the following detailed description.

DETAILED DESCRIPTION

As a major component of anchoring fibrils, collagen 7 functions in maintaining tissue integrity. Anchoring fibrils are structural elements that serve as attachment complexes at the interface between the epithelial and mesenchymal layers of several tissues, including the skin, oral mucosa, and cervix (Chung et al. *Dermatol Clin* 28(1): 93-105 (2010)). In the skin, anchoring fibrils extend from the lower portion of the epidermal basement membrane to the underlying papillary dermis, securing the association between the epidermal basement membrane and the papillary dermis (Varki et al. *J Med Genet* 44:181-192 (2007)). This association aids to provide and maintain cohesion between the epidermis and dermis, contributing to the integrity to the skin, which is critical for its proper structure, function, and homeostasis (Villone et al. *J Biol Chem* 283(36): 24506-24513 (2008)). Nucleic acid sequences encoding collagen 7 and polypeptides encoding thereby are known in the art. In one embodiment the recombinant collagen 7 is a human collagen 7.

Collagen 7 produced by recombinant methods described herein may be recovered from the host cell culture system according to standard protocols known in the art (e.g., precipitation, centrifugation, etc). Recombinant collagen 7 described herein may be secreted into the host cell medium and recovered by ammonium sulfate precipitation and subsequent centrifugation; as demonstrated in the following reference, (Chen et al. *J Bio Chem* 277(18): 2118-2124 (2002)).

Collagen 7 produced and recovered by recombinant and molecular biology methods described herein, may be purified according to standard protocols known in the art (e.g., dialysis, ion exchange chromatography, affinity chromatography, SDS gel electrophoresis, etc). The recombinant collagen 7 described herein may be purified to homogeneity by ion exchange chromatography; as demonstrated in the following reference, (Chen et al. *J Bio Chem* 277(18): 2118-2124 (2002)).

This disclosure provides a recombinant C7 (rC7) formulation containing a buffer, a non-essential amino acid, a cryoprotectant, a surfactant, and a chelating agent. In certain embodiments the non-essential amino acid is arginine, preferably L-arginine. In certain embodiments, the cryoprotectant is a sugar. In certain embodiments, the buffer comprises a phosphate buffer, such as sodium phosphate. In certain embodiments the chelating agent is citrate. In a preferred embodiment, the rC7 formulation comprises 10 mM sodium phosphate, 5 mM sodium citrate, 100 mM L-arginine, 50 mM sucrose, 70 mM NaCl, 0.05% (w/v) polysorbate-20, and pH of about 7.2.

As compared to the previously used PBS buffer, these improved formulations enhance rC7 solubility, increasing rC7 protein concentration about 8-10 fold as compared to previously used PBS buffers, and increase robustness/stability against freeze and thaw, as well as thermal stresses during storage and handling. In certain embodiments, the rC7 compositions described herein are stable for 3 months at both −65±5° C. and −20±5° C. In certain embodiments, the rC7 compositions described herein are stable for 6 months at both −65±5° C. and −20±5° C. In certain embodiments, the rC7 composition is stable for 2 weeks at 25±3° C. and up to 1 month at 5±3° C. In terms of delivery device compatibility, in certain embodiments, the rC7 composition described herein is stable for up to 8 hours at 25±3° C. when stored in disposable syringes or for up to 6 hours at 25±3° C. when diluted down to 0.1 mg/mL into saline. As used herein, "stable" means that after the indicated storage conditions, there is no significant difference in the amount of protein, as measured by absorbance at 280 nm, no significant difference in the amount of high molecular weight species, dimers, homotrimers, and low molecular weight species as measured by SEC-HPLC, and no significant loss in potency, as measured in a fibronectin binding assay.

Sugars that may be used in the compositions include, but are not limited, to non-reducing disaccharides (e.g., sucrose, trehalose) or a sugar alcohol, such as sorbitol. In certain embodiments, the sugar in the composition is sucrose.

The composition may also include one or more buffers, such as a phosphate buffer (e.g., sodium phosphate, a histidine buffer, a Tris(hydroxymethyl)aminomethane buffer.

The composition may also include one or more surfactants and/or bulking agents. Surfactants include but are not limited poloxamers (e.g., Pluronic®), polysorbates (e.g., polysorbate 80, polysorbate 20), CTAB (hexadecyltrimethylammonium bromide), or SDS (sodium dodecyl sulfate or sodium lauryl sulfate). In certain embodiments, the surfactant in the composition is a polysorbate (e.g., polysorbate 20). Bulking agents include but are not limited to PVP, PEG, dextran, mannitol and glycine.

The composition may also include one more additional pharmaceutically acceptable excipients. Examples of pharmaceutically acceptable excipients include, but are not limited to, salts, proteins (e.g., albumin), chelating agents (e.g., citrate, EDTA), gelling polymers, urea (or its derivatives), and combinations thereof.

One aspect is directed to the use of the compositions described herein to treat DEB. Also provided is a method of treating DEB comprising administering to a subject in need thereof a composition comprising recombinant collagen 7, a buffer, anon-essential amino acid, a cryoprotectant, a surfactant, and a chelating agent. In certain embodiment, the buffer is a phosphate buffer (e.g., sodium phosphate). In certain embodiments, the non-essential amino acid is arginine. In certain embodiments, the cryoprotectant is a sugar, such as sucrose. In certain embodiments the surfactant is a polysorbate, such as polysorbate 20 or polysorbate 80. In certain embodiments, the chelating agent is citrate. The amount of each component can vary as described throughout the application. In one embodiment, the composition comprises recombinant collagen 7, 10 mM sodium phosphate, 5 mM sodium citrate, 70 mM sodium chloride, 100 mM arginine, 50 mM sucrose, and 0.05% polysorbate 20 (w/v) and has a pH of 7.1 or 7.2.

EXAMPLES

Example 1

Five formulations were selected to compare freeze/thaw profiles and thermal stability, including the previously used PBS formulation. These formulations are listed in Table 1.

TABLE 1

| Formulation | Buffer | Ingredients |
|---|---|---|
| 1 | PBS, pH 7.3 | 0.5 mg/mL C7, 150 mm NaCl |
| 2 | 10 mM Phos pH 7.3 | 0.5 mg/mL C7, ~70 mM NaCl, 50 mM Arg, 50 mM Gln; 1.7% sucrose, 0.05% (v/v) Polysorbate-20, 5 mM citrate |
| 3 | 10 mM Phos pH 7.3 | 0.5 mg/mL C7, 100 mM NaCl, 50 mM Arg, 1.7% sucrose, 0.05% (v/v) Polysorbate-20, 5 mM citrate |
| 4 | 10 mM Phos pH 7.3 | 0.5 mg/mL C7, 0 mM NaCl 100 mM Arg, 1.7% sucrose, 0.05% (v/v) Polysorbate-20, 5 mM citrate |
| 5 | 20 mM Histidine/ pH 7.3 | 0.5 mg/mL C7, ~70 mM NaCl, 50 mM Arg, 1.7% sucrose, 0.05% (v/v) Polysorbate-20, 5 mM citrate |
| 6 | 10 mM TRIS pH 7.3 | 0.5 mg/mL C7, ~70 mM NaCl, 50 mM Arg, 0.05% (v/v) Polysorbate-20, 5 mM citrate |

By testing these formulations, it was discovered that L-arginine and sucrose, and preferably 75-100 mM L-arginine and 1.7% (w/v) sucrose, improved solubility. The inclusion of a surfactant (e.g., 0.05% polysorbate-20) improved filterability and is expected to lower potential non-specific adsorption. The inclusion of NaCl, and preferably about 70 mM NaCl, in the formulation improved the appearance.

The previously used rC7 formulation (PBS) only achieved solubility of upwards of 0.4 mg/mL with significant viscosity challenges above this concentration. In some cases, the PBS formulation could be pushed to upwards of 0.8 mg/mL, but only under very specific lab conditions that were not scalable or compatible with conventional protein purification processes, such as UF/DF. A formulation comprising 1 mg/mL rC7, 10 mM phosphate, 5 mM citrate, 100 mM L-arginine, 1.7% (w/v) sucrose, 70 mM NaCl, 0.05% (v/v) polysorbate-20 at pH of about 7.2 ("Phase I formulation") was able to achieve approximately ten-fold higher protein concentration (upwards of about 4 mg/mL) using conventional spin columns with a 100 kDa PES molecular weight cutoff.

Improvements in the viscosity were seen as well when compared to the PBS formulation. The PBS formulation was not able to support protein concentrations above 0.8 mg/mL. Therefore, head-to-head comparisons with higher concentration protein formulations were not possible. However, the viscosity readings for the 3 mg/mL rC7 protein formulations were all around 4 centipoise (cp), which is not considered highly viscous. These data demonstrate that in general, the increase in viscosity correlates to the increase in rC7 protein concentration. If the viscosity is compared to the protein concentration (cP/protein concentration), it becomes evident that the arginine containing formulations have lower values than those in the PBS formulation. Thus, the arginine formulations support higher protein content while better controlling increases in viscosity.

Under the intensity of a Tyndall light, the refraction of the protein and protein precipitates was significantly less for the Phase I formulation at the higher protein concentrations (upwards of 3-4 mg/mL). This gave the Phase I formulation a clearer and less turbid appearance.

The Phase I formulation was also subjected to freezing and thawing stress conditions. using a robust, small scale freeze/thaw model. The Phase I formulation was exposed to three freeze/thaw cycles (see Table 2) to reflect freeze/thaw stress that may be encountered at manufacturing scale (scalability).

TABLE 2

Freeze/Thaw (F/T) Stress Cycle for 100 mL in PETG Bottles

| Step | Ramp | Target Temp | Time |
|---|---|---|---|
| 1 | Hold | 5° C. | 30 min |
| 2 | Ramp | −5° C. | 0.2° C./min |
| 3 | Hold | −5° C. | 6 Hours |
| 4 | Ramp | −20° C. | 0.2° C./min |
| 5 | Hold | −20° C. | 6 hours |
| 6 | Ramp | 25° C. | 0.2° C./min |
| 7 | Hold | 25° C. | 3 hours |
| 8 | Ramp | 5° C. | 30 min |

Figure 4:
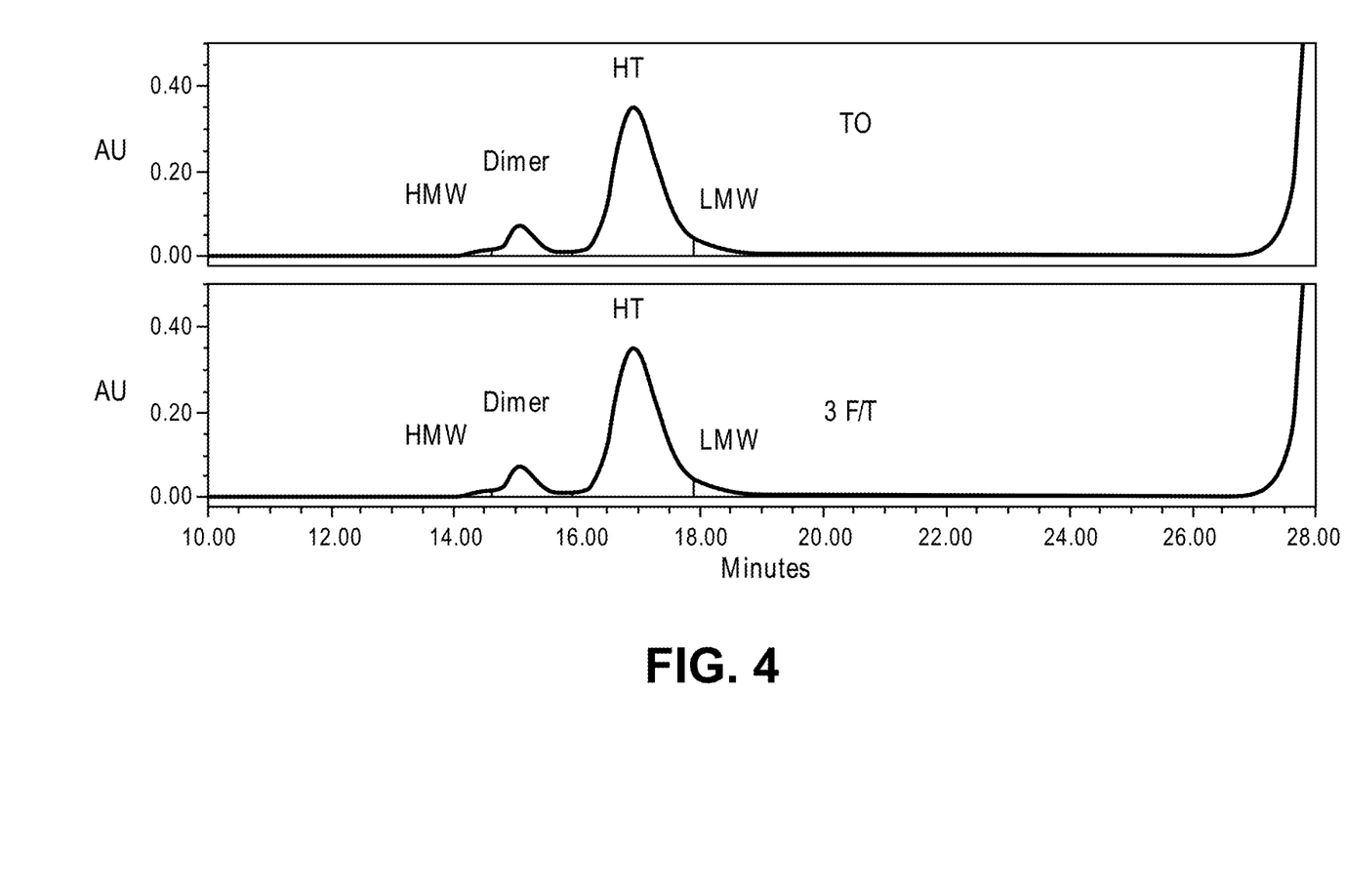
FIG. 4 shows SEC-HPLC profiles of a rC7 formulation after exposure to freeze/thaw stress.

After the 3 cycles were completed, there were no changes in either the protein content (as measured by absorbance at A280 nm; see Table 3) or in association state (as measured by SEC-HPLC; see FIG. 4).

TABLE 3

Changes After Freeze/Thaw Stress

| | A280 nm | Size Exclusion Chromatography (SEC-HPLC) | | | |
|---|---|---|---|---|---|
| | mg/mL | % HMW | % Dimer | % Homotrimer | % LMW |
| T0 | 1.0 | 1.4 | 10.7 | 78.7 | 9.2 |
| Post 3 F/T Cycles | 1.0 | 1.8 | 11.2 | 78.1 | 8.9 |

The arginine-containing formulations were subjected to 2 months of storage at temperatures of −65° C., −20° C., 5±3° C., and 25° C. There were no changes in appearance after 2 months at any storage condition. The same materials showed no significant change in protein concentration (A280 nm) or SEC-HPLC profile (see Table 4) with the exception of the formulations stored either at 5±3° C. (minimally) or 25° C. After 2 months storage at 25° C., an increase (~2%) in high molecular weight (HMW) species was seen.

TABLE 4

Changes After Storage for Two Months at Various Temperatures

| | A280 (nm) | SEC-HPLC | | | |
|---|---|---|---|---|---|
| Sample | mg/mL | % HMW | % Dimer | % HT | % LMW |
| T0 | | | | | |
| ≤−65° C. | 1.1 | 1.6 | 9.9 | 77.3 | 11.2 |
| −20° C. | 1.1 | 1.7 | 10.2 | 76.8 | 11.4 |
| 5° C. | 1.1 | 2.3 | 12.4 | 74.4 | 10.9 |
| 25° C. | 1.1 | 4.1 | 18.0 | 67.5 | 10.4 |

The Phase I formulation at a 1 mg/mL dose was also assessed for compatibility with the animal delivery devices and dosing syringes. The 1 mg/mL drug product was injected into the infusion set(s) with the appropriate syringe(s), and the drug held for up to 60 minutes in each of the devices. There were no visible particles or pH shifts after 60 minutes in the devices. The SEC-HPLC profiles also demonstrated no significant changes It is difficult to know what happens when rC7 is injected IV into the bloodstream. It is possible, however, to assess the potential for product quality changes by monitoring for any changes when the protein is exposed to more physiologically relevant conditions such as buffers containing 10% bovine serum and held at 37° C. The rC7 protein is prone to soluble aggregation and precipitation. These events can be monitored through common analytical techniques. The A280 absorbance is used to monitor for changes in protein content. The A320 absorbance is used to monitor for changes in turbidity due to insoluble particulate formation. SEC-HPLC is used to monitor for changes in the soluble protein where HMW and/or LMW species may form. To maximize the impact of the serum effect, the buffers were diluted with equal parts serum and incubated in the presence of rC7 (in the Phase I formulation) at a final protein concentration of 0.5 mg/mL. To simulate body temperature, all samples were held for 1 hour at 37° C. The summary of these results are listed in Table 5. The results demonstrated no changes in protein content (A280), or turbidity (A320), after exposure to physiological media for 1 hour at 37° C. Thus, the data suggest there are no apparent immediate solubility limitations upon dilution of rC7 delivery into serum.

TABLE 5

A280 and A320 Absorbance after 1 hour at 37° C. exposure

| | Initial (A280/mm) | 1 hr at 37° C. (A280/mm) | Initial (A320/mm) | 1 hr at 37° C. (A320/mm) |
|---|---|---|---|---|
| Water | 0.00145 | 0.00134 | 0.00090 | 0.00097 |
| Placebo in PBS + Ca | 0 | 0.00215 | 0.00127 | 0.00138 |
| Placebo in PBS no Ca | 0.00375 | 0.00225 | 0.00221 | 0.00108 |
| Placebo in PBS + Ca and 10% serum | 0.32405 | 0.31336 | 0.01319 | 0.0131 |
| Placebo in PBS no Ca and 10% serum | 0.32068 | 0.31129 | 0.01363 | 0.01267 |
| 0.5 mg/mL C7 in PBS + Ca | 0.02896 | 0.03234 | 0.00188 | 0.00224 |
| 0.5 mg/mL C7 in PBS no Ca | 0.03134 | 0.03139 | 0.00210 | 0.00184 |
| 0.5 mg/mL C7 in PBS + Ca and 10% serum | 0.33182 | 0.33807 | 0.01321 | 0.01345 |
| 0.5 mg/mL C7 in PBS no Ca and 10% serum | 0.34846 | 0.33424 | 0.01386 | 0.01338 |
| 90% PBS + 10% serum (control) | n/a | 0.31847 | N/A | 0.01343 |

To see if calcium and magnesium had an effect on changes in product quality, the starting Dulbecco's phosphate buffered saline (D-PBS) was obtained without the inclusion of $Ca^{2+}$ and $Mg^{2+}$ cations in the buffer. This solution was tested and compared to D-PBS where physiological levels of $Ca^{2+}$ and $Mg^{2+}$ were added. These were found to have no effect on the results (Table 5).

Figure 5:
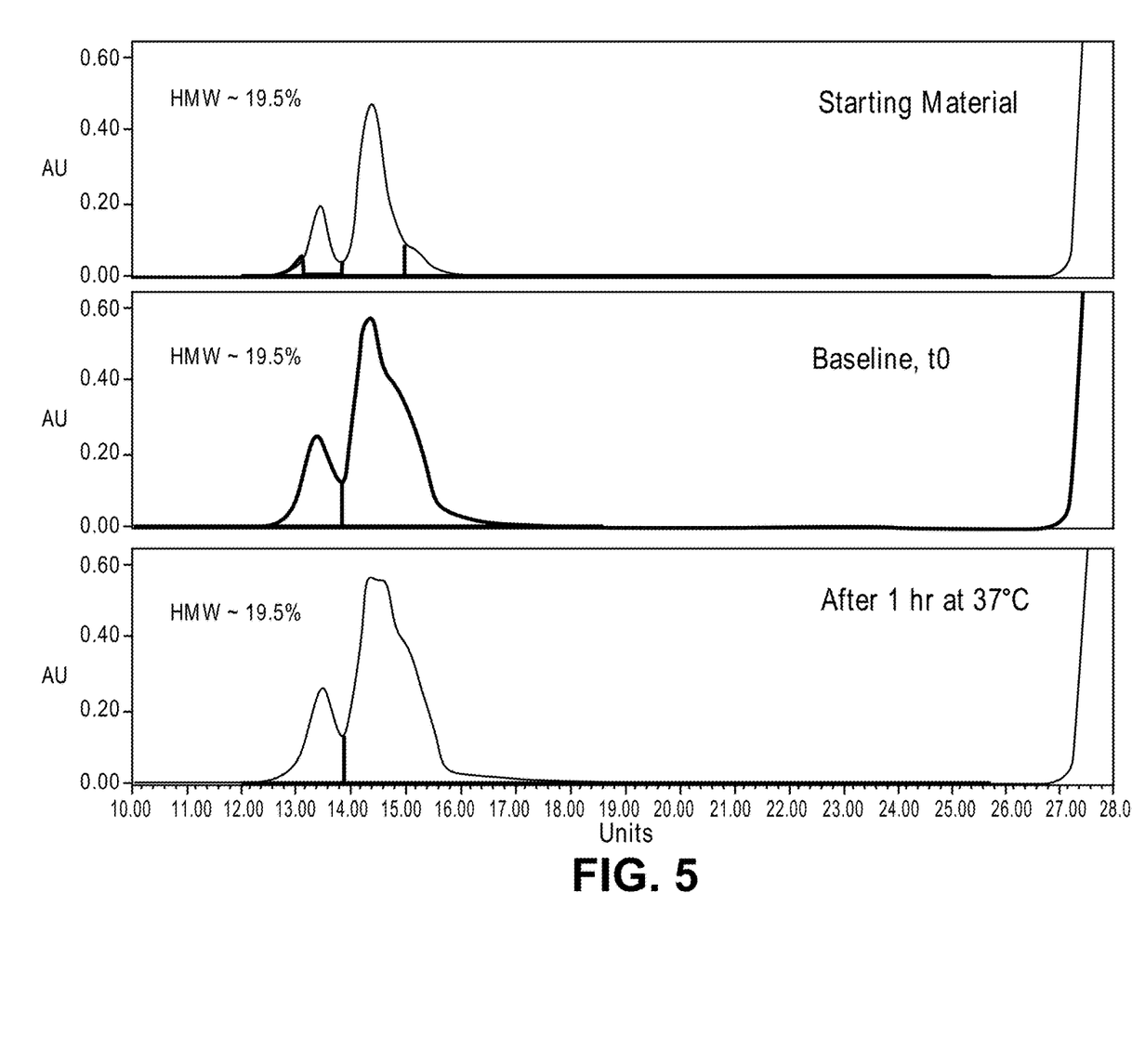
FIG. 5 shows SEC-HPLC for 0.5 mg/mL rC7 diluted in D-PBS and 10% serum after incubation for 1 hour at 37° C.

The SEC-HPLC profiles confirmed that after 1 hour exposure to the various test buffer matrices at 37° C., there were no increases in insoluble aggregates. FIG. 5. The exposure to the various buffers triggers an initial change in the lower molecular weight region of the peak, likely due to an increase in the flexibility of the α-helix.

Figure 6:
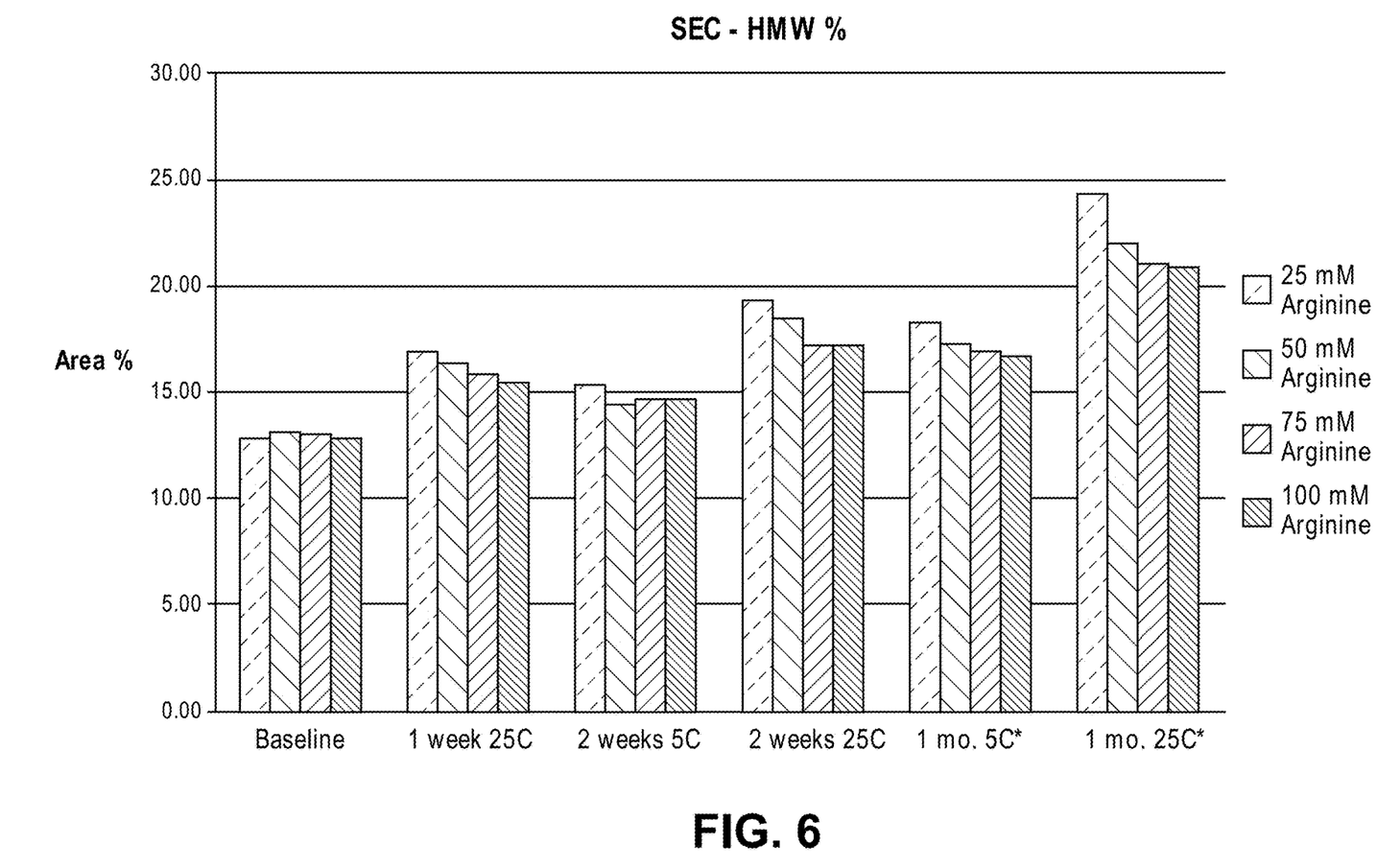
FIG. 6 shows % HMW species of rC7 formulations containing different amounts of arginine after storage at various temperatures.
Figure 7:
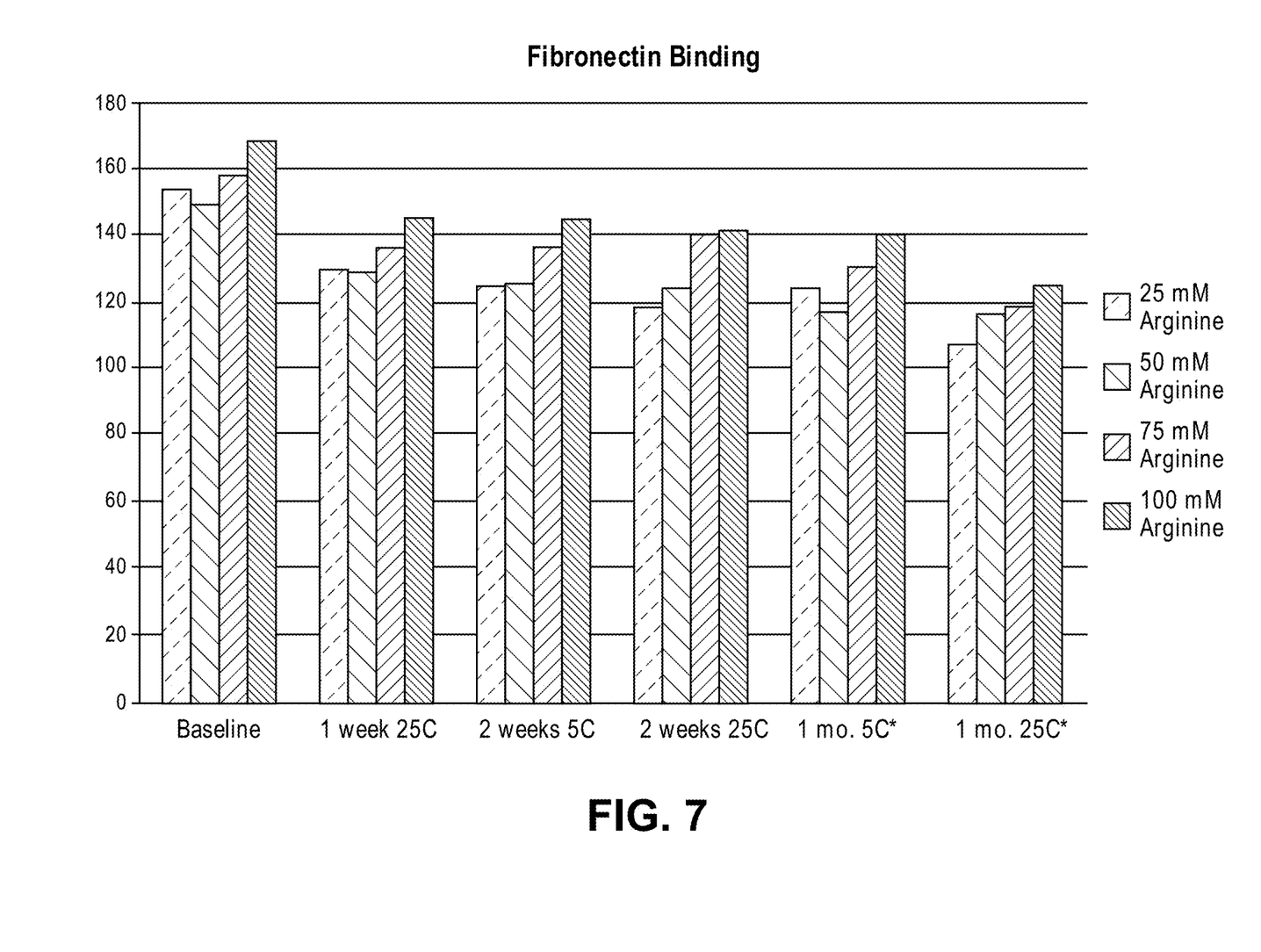
FIG. 7 shows fibronectin binding of rC7 formulations containing different amounts of arginine after storage at various temperatures.

Thermal stability studies were conducted on rC7 formulations containing different amounts of L-arginine (25 mM to 100 mM). The results show that lowering the L-arginine level leads to a slight increase in high molecular weight species and decreased potency (as measured by a fibronectin binding assay) after storage for up to one month at both 5±3° C. and 25±3° C. FIG. 6 and FIG. 7. Additionally, more opalescence was seen in the samples at 25 mM and 50 mM arginine. Other excipient levels were kept the same in these studies.

Example 2

Based on initial development studies, a formulation containing 10 mM sodium phosphate, 5 mM sodium citrate, 70 mM sodium chloride, 100 mM arginine, 50 mM sucrose, 0.05% polysorbate 20, and pH of about 7.1 was used for administration to Col7a1−/− mice in a mouse model of DEB.

Recombinant human collagen 7 (rC7) was produced in CHO cells. rC7 was purified from the CHO cells using two different manufacturing processes. A rC7 lot produced from each manufacturing process was formulated in a composition comprising 10 mM sodium phosphate, 5 mM sodium citrate, 70 mM sodium chloride, 100 mM arginine, 50 mM sucrose, 0.05% polysorbate 20, and pH of about 7.1.

The study was conducted in a total of 59 neonatal Col7a1−/− mice across 3 treatment groups to evaluate distribution and histological improvement following a single IV administration of rC7 on postnatal day 2-3. Overall survival was additionally examined in this study. Each composition (test article 1 and test article 2) was administered intravenously at a dosage of 0.4 mg/mL (16 μg in 40 μL) to 26 neonatal Col7a1−/− mice. The compositions were administered as a single IV bolus via the superficial temporal vein on postnatal day 2-3. A control composition comprising 10 mM sodium phosphate, 5 mM sodium citrate, 70 mM sodium chloride, 100 mM arginine, 50 mM sucrose, 0.05% polysorbate 20, and pH of about 7.1—but without rC7 was also intravenously administered to neonatal Col7a1−/− mice.

Figure 1:
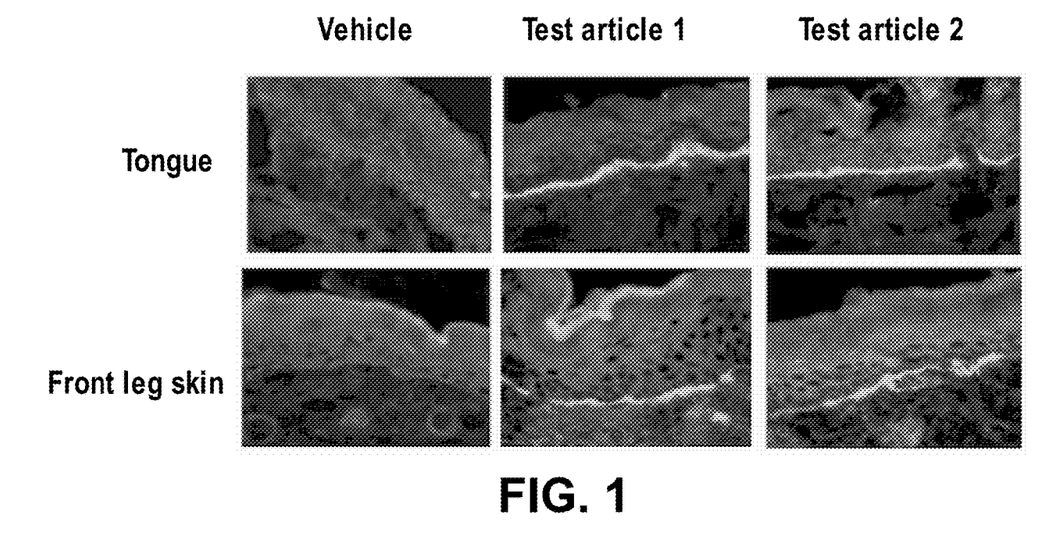
FIG. 1 shows representative immunofluorescent images in tongue and front leg from Col7a1−/− mice surviving 5-7 days following administration of rC7 compositions or a control.

Administration of test article 1 and test article 2 resulted in the distribution of rC7 to the dermal-epidermal BMZ in tongue and front leg skin in the neonatal Col7a1−/− mice. FIG. 1. In contrast, C7 was not detected in any mouse injected with vehicle control. FIG. 1.

Figure 2:
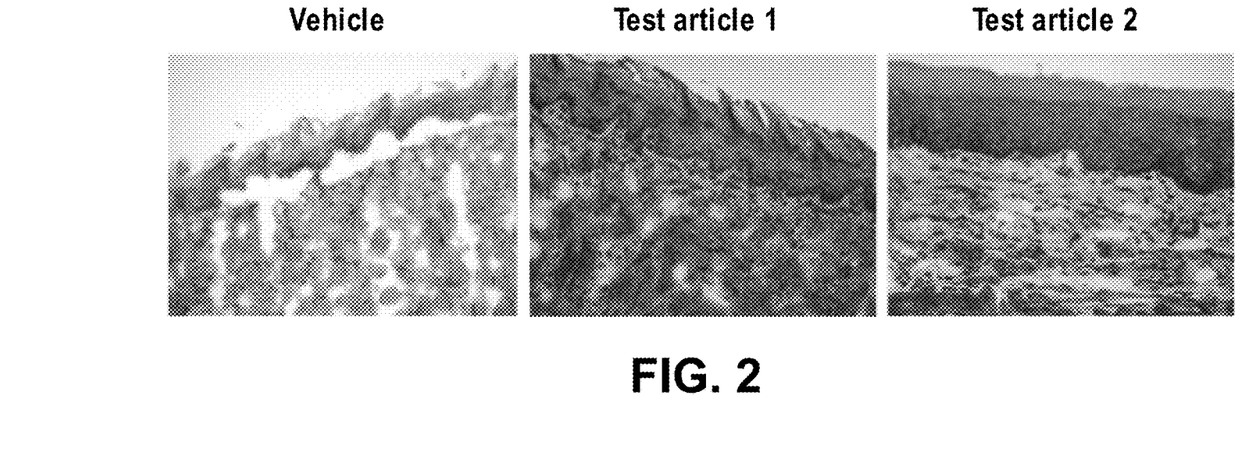
FIG. 2 shows representative H&E staining in tongue from Col7a1−/− mice following administration of rC7 compositions or a control.

Intravenous administration of the test compositions resulted in correction of dermal-epidermal separation in Col7a1−/− mice compared to vehicle control, as demonstrated by representative hematoxylin and eosin (H&E) images of tongue tissue sections. FIG. 2. The tongue is the optimal tissue to examine dermal-epidermal separation due to the lack of hair, which can serve to anchor the epidermis to the dermis and prevent the formation of newly induced blisters.

The proportion of mice with complete closure (i.e., no separation) between the epidermis and dermis in tongue was 50% (12 out of 26), 63% (15 out of 26), and 10% (1 out of 10) for Col7a1−/− mice administered test article 1, test article 2, and vehicle control, respectively. The proportion of Col7a1−/− mice with complete closure of dermal-epidermal separation was higher in rC7 treated mice than vehicle control (test article 1 vs vehicle Fisher p=0.06, test article 2 vs vehicle Fisher p=0.02). The proportion of Col7a1−/− mice with closure of dermal-epidermal separation did not differ between rC7 treated mice (Fisher p=0.58).

Figure 3:
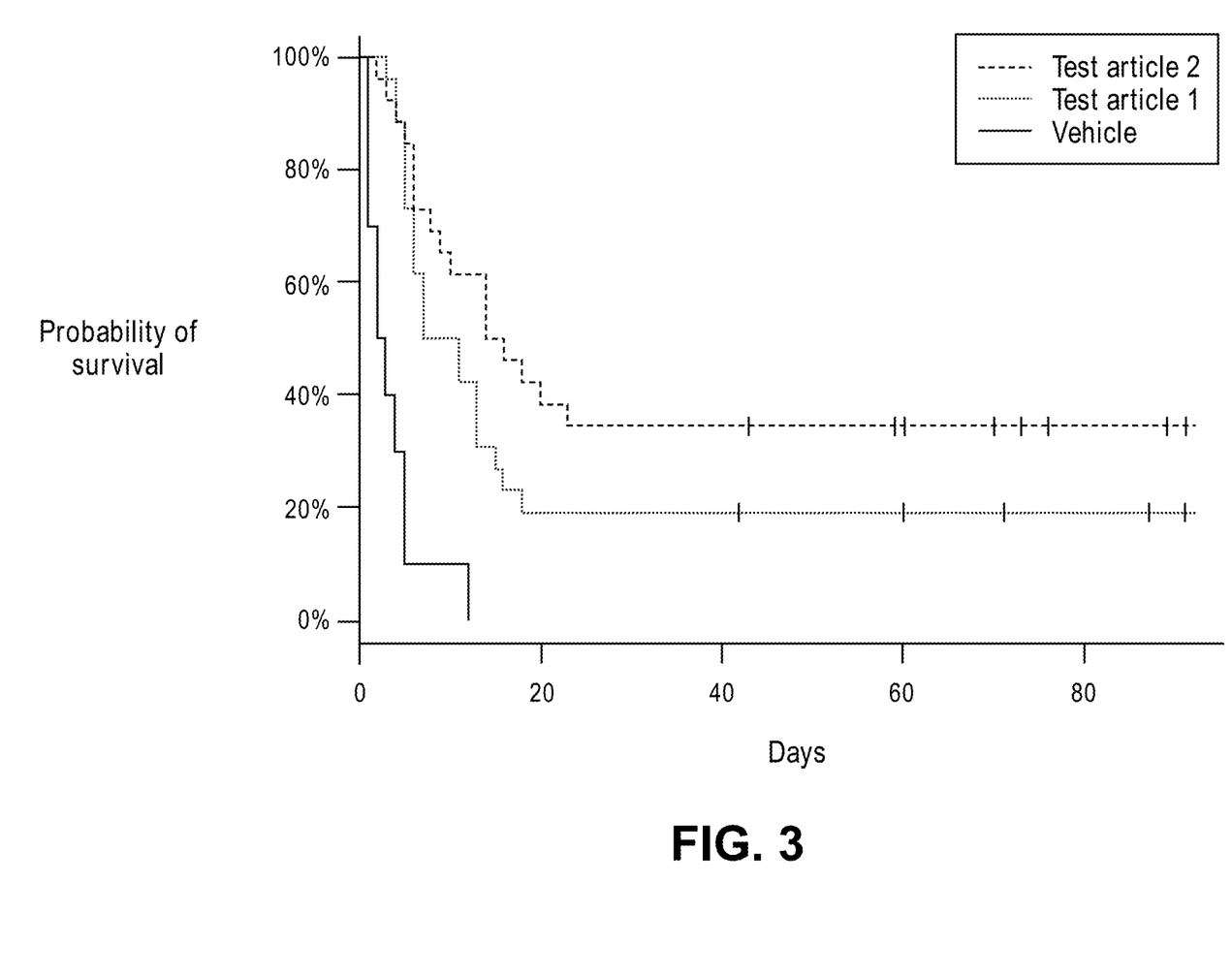
FIG. 3 is a Kaplan-Meier Curve showing the probability of survival of Col7a1−/− mice following administration of rC7 compositions or a control.

A single IV administration of test article 1 or 2 to neonatal Col7a1−/− mice resulted in a statistically significant improvement in survival compared to vehicle controls, as shown in Table 7 below and FIG. 3. The median (interquartile-range) survival time was 2.5, 9, and 14 days for Col7a1−/− mice administered vehicle control, test article 1, and test article 2, respectively.

TABLE 6

| Hazard Ratios Comparing Treatment Groups | | | |
| --- | --- | --- | --- |
| Comparison | Hazard Ratio | 95% Confidence Interval | P Value |
| Test Article 1 versus Vehicle | 0.18 | 0.08-0.40 | <0.001 |
| Test Article 2 versus Vehicle | 0.11 | 0.05-0.25 | <0.001 |
| Test Article 1 versus Test Article. 2 | 1.66 | 0.87-3.15 | 0.13 |

In Table 6, hazard ratios were estimated in a Cox proportional hazards model. The proportional hazards assumption was satisfied as assessed by Schoenfeld residuals (p>0.37).

This study demonstrated efficacy for the tested rC7 compositions in a neonatal murine model of DEB. Specifically, both test articles distributed to the dermal-epidermal BMZ in tongue and skin, corrected dermal-epidermal separation, and resulted in a statistically significant improvement in survival compared to vehicle control following a single IV injection in Col7a1−/− mice.

To support Phase I/II clinical trials of Dystrophic Epidermolysis Bullosa (DEB) program, the following drug substances/drug products will be used: Drug Substance (DS)—Frozen liquid with 500 mL fill in 1 L polycarbonate (PC) bottle with rC7 at 1.0 mg/mL; Drug Product (DP)—Frozen liquid with 5.5 mL fill in 10 cc glass vial with rC7 at 1.0 mg/mL. The formulation comprises 10 mM sodium phosphate, 5 mM sodium citrate, 100 mM L-arginine, 50 mM sucrose, 70 mM NaCl, 0.05% (w/v) polysorbate-20, pH of about 7.2.

In terms of long-term storage stability, for DS, to date, GMP material is stable for 3 months at both −65±5° C. and −20±5° C., with no significant change in the protein concentration, as measured by absorbance at 280 nm, no significant change in the amount of high molecular weight species, dimers, homotrimers, and low molecular weight species as measured by SEC-HPLC, and no significant change in potency, as measured in a fibronectin binding assay. For DP, to date, development lots are stable for 6 months at both −65±5° C. and −20±5° C. For handling, the formulation is stable for 2 weeks at 25±3° C. and up to 1 month at 5±3° C. Care should be taken to minimize exposure from light, prevent excessive shaking during product handling. In terms of delivery device compatibility, the formulation is stable for up to 8 hours at 25±3° C. when stored in disposable syringes or for up to 6 hours at 25±3° C. when rC7 is diluted down to 0.1 mg/mL into saline. Furthermore, no changes in protein content were observed in the presence of PBS containing 10% bovine serum after storage for 1 hour at 37° C. This indicates physiological compatibility of the drug product upon administration.

While one or more exemplary embodiments have been described in the specification, it will be understood by those of ordinary skill in the art that various changes in form and details may be made therein without departing from the spirit and scope of the inventive concept as defined by the claims that follow.

REFERENCES

1. Fine J D, Bauer E A, Gedde-Dahl, T (1999). Inherited epidermolysis bullosa: definition and historical overview. In: Fine J D, Bauer E A, McGuire J, Moshell A, eds. Epidermolysisbullosa: Clinical, epidemiologic, and laboratory advances, and the findings of the National Epidermolysis Bullosa Registry. Baltimore: Johns Hopkins University Press; 1999:1-19.
2. Fine J D, Eady R A, Bauer E A, et al. The classification of inherited epidermolysis bullosa (EB): Report of the Third International Consensus Meeting on Diagnosis and Classification of EB. J Am Acad Dermatol. 2008 June; 58(6):931-50.
3. Bruckner-Tuderman L. Dystrophic epidermolysis bullosa: Pathogenesis and clinical features. Dermatol Clin. 2010 January; 28(1):107-14.
4. Pfendner E G, Lucky A W. Dystrophic Epidermolysis Bullosa. 2006 Aug. 21 [Updated 2010 Nov. 4]. In: Pagon R A, Adam M P, Bird T D, et al., editors. GeneReviews™ [Internet]. Seattle (Wash.): University of Washington, Seattle; 1993-2013.
5. Dang N, Murrell D F. Mutation analysis and characterization of COL7A1 mutations in dystrophic epidermolysis bullosa. Exp Dermatol. 2008 July; 17(7):553-68.
6. Heinonen S. Targeted inactivation of the type VII collagen gene (Col7a1) in mice results in severe blistering phenotype: a model for recessive dystrophic epidermolysis bullosa. J Cell Sci. 1999 November; 112(21):3641-8.

What is claimed is:

1. A composition comprising recombinant collagen 7, 10 mM sodium phosphate, 5 mM sodium citrate, 70 mM sodium chloride, 75 mM to 100 mM arginine, 50 mM sucrose, and 0.05% polysorbate 20.
2. The composition of claim 1, wherein the composition has a pH of between 7.0-7.2.
3. The composition of claim 1, wherein the recombinant collagen 7 is human collagen 7.
4. A pharmaceutical composition comprising recombinant collagen 7, 10 mM sodium phosphate, 5 mM sodium citrate, 70 mM sodium chloride, 75 mM to 100 mM arginine, 50 mM sucrose, and 0.05% polysorbate 20 and one or more pharmaceutically acceptable excipients.
5. The composition of claim 4, wherein the composition has a pH of between 7.0-7.2.
6. The composition of claim 4, wherein the recombinant collagen 7 is human collagen 7.
7. The composition of claim 6, wherein the composition is stable for:
   (a) 3 months at −65±5° C., or −20±5° C., when 500 mL of the composition is stored in a 1 liter polycarbonate bottle;
   (b) 6 months at −65±5° C., or −20±5° C., when 5.5 mL of the composition is stored in a 10 glass vial;
   (c) 2 weeks at 20±5° C.; and/or
   (d) up to 1 month at 5±3° C.
8. The composition of claim 6, for use in the treatment of dystrophic epidermolysis bullosa.
9. A method of treating dystrophic epidermolysis bullosa, comprising administering to a subject in need thereof an effective amount of a composition comprising recombinant collagen 7, 10 mM sodium phosphate, 5 mM sodium citrate, 70 mM sodium chloride, 75 mM to 100 mM arginine, 50 mM sucrose, and 0.05% polysorbate 20, wherein the administration is through intravenous injection.
10. The composition of claim 2, wherein the recombinant collagen 7 is human collagen 7.
11. The composition of claim 5, wherein the recombinant collagen 7 is human collagen 7.
12. The method of claim 9, wherein the recombinant collagen 7 is human collagen 7.
13. The method of claim 9, wherein the composition has a pH between 7.0-7.2.
14. The method of claim 13, wherein the composition is stable for:
   (a) 3 months at −65±5° C., or −20±5° C., when 500 mL of the composition is stored in a 1 liter polycarbonate bottle;
   (b) 6 months at −65±5° C., or −20±5° C., when 5.5 mL of the composition is stored in a 10 glass vial;
   (c) 2 weeks at 20±5° C.; and/or
   (d) up to 1 month at 5±3° C.
15. The composition of claim 2 or 5, wherein the composition comprises recombinant collagen 7, 10 mM sodium phosphate, 5 mM sodium citrate, 70 mM sodium chloride, 100 mM arginine, 50 mM sucrose and 0.05% polysorbate 20, and wherein the composition has a pH of 7.1 or 7.2.
16. The method of claim 13, wherein the composition has a pH 7.1 or 7.2.
17. The composition of claim 15, wherein the composition comprises recombinant collagen 7 at 1.0 to 4.0 mg/mL.
18. The method of claim 9, wherein the composition comprises recombinant collagen 7 at 1.0 to 4.0 mg/mL.

* * * * *